United States Patent [19]
Scott

[11] Patent Number: 5,414,168
[45] Date of Patent: May 9, 1995

[54] ABSORPTION AND COLD SEPARATION PROCESS FOR RECOVERING PURIFIED HYDROGEN FROM A CATALYTIC DEHYDROGENATION ZONE EFFLUENT

[75] Inventor: Norman H. Scott, Arlington Heights, Ill.

[73] Assignee: UOP, Des Plaines, Ill.

[21] Appl. No.: 57,400

[22] Filed: May 6, 1993

Related U.S. Application Data
[62] Division of Ser. No. 996,204, Dec. 23, 1992.

[51] Int. Cl.$^6$ .......................... C07C 7/20; C07C 5/23; F25J 3/06; C10G 9/00
[52] U.S. Cl. .......................................... 585/2; 585/6; 585/655; 585/809; 62/11; 62/23; 208/101; 208/102; 208/103
[58] Field of Search ...................... 585/2, 6, 655, 809; 62/11, 23; 208/101, 102, 103

[56] References Cited

U.S. PATENT DOCUMENTS

| | | | |
|---|---|---|---|
| 3,882,014 | 5/1975 | Monday et al. | 208/134 |
| 4,212,726 | 7/1980 | Mayes | 208/101 |
| 4,333,820 | 6/1982 | Scheijele, Jr. | 585/655 |
| 4,381,418 | 4/1983 | Gewartowski et al. | 585/655 |

*Primary Examiner*—Anthony Mc Farlane
*Assistant Examiner*—Nhat D. Phan
*Attorney, Agent, or Firm*—Thomas K. McBride; John F. Spears, Jr.; Reginald K. Taylor

[57] ABSTRACT

Purified hydrogen is recovered from the effluent of a catalytic dehydrogenation zone using an integrated cold absorption process. The effluent, which contains olefinic hydrocarbons and hydrogen is compressed, cooled and contacted with a liquid absorbent. The purified hydrogen can be recycled to the dehydrogenation zone and the olefinic hydrocarbons are recovered as product. The present invention will recover higher purity hydrogen and liquefiable hydrocarbons more economically than prior art processes.

7 Claims, 1 Drawing Sheet

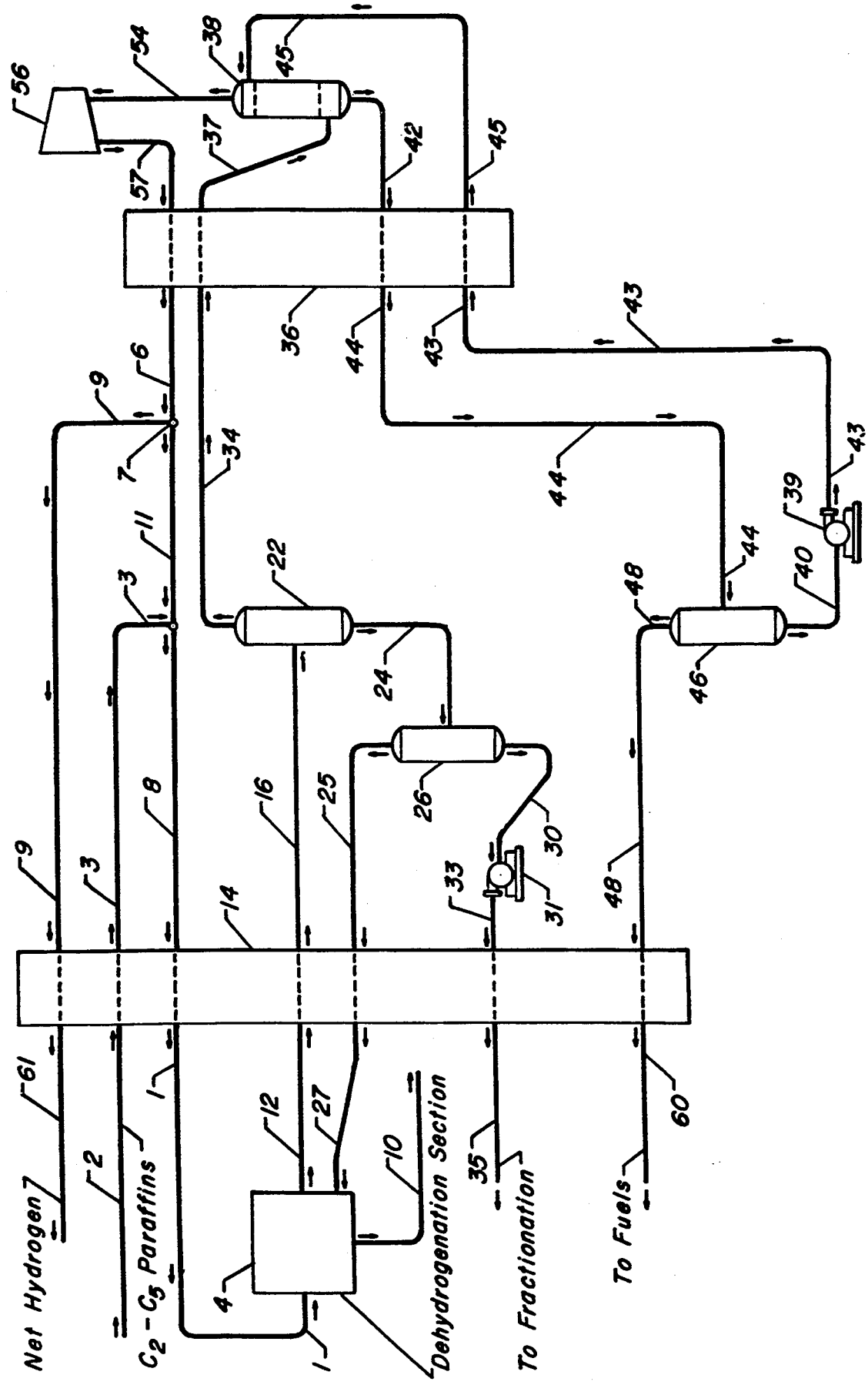

ABSORPTION AND COLD SEPARATION PROCESS FOR RECOVERING PURIFIED HYDROGEN FROM A CATALYTIC DEHYDROGENATION ZONE EFFLUENT

CROSS REFERENCE TO RELATED APPLICATION

This application is a division of prior copending application Ser. No. 07/996,204 filed Dec. 23, 1992, the contents of which are incorporated herein by reference thereto.

FIELD OF THE INVENTION

The present invention is related to a method of separating a hydrogen-containing gas stream into a relatively hydrocarbon-free, hydrogen-rich stream and a relatively hydrogen-free, hydrocarbon stream.

BACKGROUND OF THE INVENTION

Various types of catalytic hydrocarbon conversion reaction systems have found widespread utilization throughout the petroleum and petrochemical industries for effecting the conversion of hydrocarbons to different products. Moreover, such systems often result in either the net production or the net consumption of hydrogen. As applied to petroleum refining, these reaction systems have been employed to effect numerous hydrocarbon conversion reactions, including catalytic reforming and catalytic dehydrogenation of paraffins.

Catalytic dehydrogenation of $C_2$-$C_5$ hydrocarbons is well known in the petroleum industry. The monoolefinic hydrocarbon products derived therefrom are generally useful as intermediates in the production of other more valuable hydrocarbon conversion products.

Catalytic dehydrogenation can be combined with other catalytic hydrocarbon conversion processes to produce a variety of useful products. For example, the olefins produced during catalytic dehydrogenation of a liquid petroleum gas stream containing isobutane can be used in conjunction with an etherification unit wherein isobutylene is reacted with methanol to produce methyl-t-butyl ether (MTBE). Another example of combining catalytic dehydrogenation of hydrocarbons with other hydrocarbon conversion processes is the use of propylene and butylenes produced from dehydrogenation in an HF alkylation unit wherein these olefins are alkylated with isobutane to produce a high octane motor fuel.

The separation of a hydrogen-rich gas stream from the effluent of a catalytic hydrocarbon conversion process is well known in the art. It is important to separate the hydrogen-rich gas stream from the catalytic conversion effluent for several reasons:

(1) catalytic conversion reactions generally require the presence of hydrogen and recycling the processed-derived, hydrogen-rich gas stream to the catalytic conversion reaction zone is cost effective;

(2) any excess processed-derived, hydrogen-rich gas can be used in other catalytic hydrocarbon conversion processes located at the refinery; and (3) it is particularly desirable not to lose product olefins or unreacted feed hydrocarbons in the product hydrogen.

An example of a process for separating a hydrogen-rich gas stream from a catalytic reforming effluent can be found in U.S. Pat. No. 3,520,799 (Forbes). This patent discloses a method of obtaining a high purity hydrogen gas stream from a catalytic reforming effluent by passing the effluent to a low pressure vapor-liquid equilibrium separation zone from which there is produced a hydrogen-containing gas stream and a liquid hydrocarbon stream. After compression, the hydrocarbon-containing gas stream is recontacted with the liquid hydrocarbon stream and the resulting mixture is passed to a high pressure vapor-liquid equilibrium separation zone. A second hydrogen-containing gas stream is produced having a higher hydrogen purity than the first. A portion of this second hydrogen-containing gas stream is passed into an absorption zone where it is contacted with a lean sponge oil, preferably comprising $C_6^+$ hydrocarbons. A third hydrogen-containing gas stream is removed from the absorption zone and, after cooling, passed to a third vapor-liquid equilibrium separation zone. The sponge oil is removed from the absorption zone and is admixed with the liquid hydrocarbon stream from the low pressure vapor-liquid equilibrium separation zone prior to recontacting thereof with the compressed hydrogen-containing gas stream. A hydrogen-rich gas stream is removed from the third vapor-liquid equilibrium separation zone.

U.S. Pat. No. 3,882,014 (Monday et al.) also discloses a method of obtaining a high purity hydrogen gas stream from a catalytic reforming effluent. The effluent is first passed to a vapor-liquid equilibrium separation zone from which there is recovered a liquid hydrocarbon stream and a hydrogen-containing gas stream. After compression, the hydrogen-containing gas stream is passed to an absorption zone wherein it is contacted with a sponge oil comprising stabilized reformate. A hydrogen-rich gas stream is recovered from the absorption zone with one portion thereof being recycled to the reforming zone while the remainder is recovered for use in other hydrocarbon conversion processes.

U.S. Pat. No. 4,212,726 (Mayes) discloses another method of recovering hydrogen-rich gas streams from catalytic reforming reaction zone effluents wherein the reaction zone effluents from the catalytic reforming process are passed to a first vapor-liquid equilibrium separation zone from which is recovered a first hydrocarbon liquid stream and a first hydrogen-containing gas stream. After compression, the hydrogen-containing gas stream is passed to an absorption column where it is contacted with the first liquid hydrocarbon from the vapor-liquid equilibrium separation zone and stabilized reformate. A hydrogen-rich gas stream is recovered from the absorption zone with one portion being recycled back to the catalytic reforming reaction zone and the balance being recovered for use in other hydrocarbon conversion processes.

In all of the above patented processes, the catalytic hydrocarbon conversion effluent from which the hydrogen-rich gas stream is recovered is an effluent from a catalytic reforming reaction zone whereas in the present invention the catalytic hydrocarbon conversion effluent from which the hydrogen-rich gas stream is recovered is an effluent from a catalytic dehydrogenation reaction zone. There are significant differences in reactions, feedstocks, operating conditions and effluents between reforming and dehydrogenation processes.

Catalytic reforming reactions are numerous and varied. For example, the catalyst and operating conditions used in reforming promote the formation of higher octane unsaturated cyclic compounds such as aromatics by dehydrogenation of naphthenes, isomerization of paraffins and naphthenes, dehydrocyclization of paraffins, and hydrocracking. However, in a catalytic dehydrogenation zone, only one reaction is predominant, that reaction being dehydrogenation of paraffins to produce olefins.

Reforming feedstocks contain a mixture of hydrocarbon components that typically have a boiling point range of about 100° F. to about 400° F. In contrast, dehydrogenation feedstocks are typically made up of pure components of methane (b.p. −127.5° F.), propane (b.p. −43.7° F.), isobutane (b.p. 10.9° F.) and isopentane (b.p. 82.1° F.), each having much lower boiling points.

The effluent from a reforming reaction zone contains a significant amount of normally liquid hydrocarbons such as benzene, toluene and xylenes. Accordingly, a suitable separation of the hydrogen-rich gas stream from the catalytic hydrocarbon conversion effluent can generally be effected by condensing out the hydrocarbons and absorbing the hydrogen-containing gas with lean oil at relatively mild conditions of temperature and pressure. For instance, in the Forbes and Mayes patents, the absorber temperatures are about 90°-150° F. Further, in the Monday et al. patent, the absorber temperature is about 100° F.

In contrast, the dehydrogenation effluent contains a significant amount of lower molecular weight olefinic hydrocarbons that are normally in the gaseous state. Accordingly, the operating conditions, particularly the absorber temperature, must be substantially lower to accomplish effective separation of a hydrogen-rich gas stream from a dehydrogenation effluent.

U.S. Pat. No. 4,381,418 (Gewartowski et al.) discloses a process for recovering a hydrogen-rich gas stream from the effluent of a catalytic dehydrogenation reaction zone comprising compressing the dehydrogenation effluent stream and cooling by indirect heat exchange using catalytic dehydrogenation feedstock comprising a hydrogen/hydrocarbon admixture, forming a hydrogen-containing gas stream and a liquid hydrocarbon stream, separating the hydrogen-containing gas stream and the liquid hydrocarbon stream, cooling the hydrogen-rich gas stream by gas expansion to form a hydrogen-rich gas stream, combining one portion of the hydrogen-rich gas stream with a paraffinic hydrocarbon stream to form the catalytic dehydrogenation feedstock admixture referred to above and recovering the other portion of said hydrogen-rich gas stream. Nowhere in Gewartowski et al. is there disclosed or suggested contacting a hydrogen-containing gas stream with a liquid absorbent.

SUMMARY OF THE INVENTION

It has been discovered that integrating a cold temperature absorption zone into a dehydrogenation effluent separation process can effectively recover a relatively hydrocarbon-free, hydrogen-rich gas stream for recycle to the dehydrogenation reaction zone or for use in other hydrocarbon conversion reaction zones. The present invention will recover higher purity hydrogen and liquefiable hydrocarbons more economically than prior art processes. It is important that the hydrogen-rich stream recycled to the dehydrogenation reaction zone contain only a minimal amount of hydrocarbons for several reasons:

(1) in equilibrium reaction systems, such as is the case with the dehydrogenation of $C_2$–$C_5$ hydrocarbons, higher conversion results from having a minimal amount of olefinic hydrocarbon product admixed with the feed;

(2) smaller and less expensive reactors can be employed if the recycle hydrogen is relatively hydrocarbon-free;

(3) there is a reduction in product losses in the net hydrogen stream as shown herein wherein the net hydrogen and recycle gas have the same origin and hence the same composition; and (4) in the dehydrogenation zone, lower utilities are associated with the use of a charge heater and lower capital investment is associated with the combined feed heat exchanger.

As used herein, the terms hydrogen-rich and methane-rich are intended to represent relative hydrogen and methane concentrations in a particular stream in comparison to the hydrogen and methane concentration in other streams in the process of the present invention.

The present invention is a process for producing a hydrogen-rich gas stream by treating an effluent comprising hydrogen and at least about 20 to 60 mole % $C_2$–$C_5$ olefinic hydrocarbons from a catalytic dehydrogenation conversion reaction zone comprising the steps of: cooling the dehydrogenation effluent by indirect heat exchange with a stream comprising at least a portion of the hydrogen-rich gas stream; passing the effluent to a first vapor-liquid separation zone and recovering therefrom a hydrogen-containing vapor phase and a liquid phase comprising $C_2$–$C_5$ olefinic hydrocarbons; contacting the hydrogen-containing vapor phase with a lean liquid absorbent comprising $C_2$–$C_5$ hydrocarbons in an absorption zone to produce the hydrogen-rich gas stream and a methane-rich liquid absorbent; refrigerating the hydrogen-rich gas stream and passing the refrigerated hydrogen-rich gas stream in indirect heat exchange with the hydrogen-containing vapor phase; and recovering the hydrogen-rich gas stream.

In one embodiment, the present invention is a process for producing a hydrogen/hydrocarbon admixture for use in a catalytic dehydrogenation reaction zone by treating an effluent of the dehydrogenation zone, the effluent comprising at least about 20 to 60 mole % $C_2$–$C_5$ olefinic hydrocarbons, comprising the steps of: cooling the effluent by indirect heat exchange with the admixture; passing the effluent to a first vapor-liquid separation zone and recovering therefrom a hydrogen-containing vapor phase and a liquid phase comprising $C_2$–$C_5$ olefinic hydrocarbons; contacting the hydrogen-containing vapor phase with a lean liquid absorbent comprising $C_2$–$C_5$ hydrocarbons at a temperature of less than about −120° F. in a countercurrent absorption zone to produce a hydrogen-rich gas stream and a methane-rich liquid absorbent; refrigerating the hydrogen-rich gas stream to a temperature of less than about −250° F. and passing the refrigerated hydrogen-rich gas stream in indirect heat exchange with the hydrogen-containing vapor phase; admixing the hydrogen-rich gas stream with a hydrocarbon liquid comprising $C_2$–$C_5$ paraffins to form the admixture; and recovering the admixture.

In another embodiment, the present invention is a process for the catalytic dehydrogenation of an admixture comprising hydrogen and at least about 20 to 60 mole % $C_2$–$C_5$ paraffinic hydrocarbons comprising the steps of: contacting the admixture with a dehydrogenation catalyst in a dehydrogenation zone at dehydrogenation conditions to produce an effluent stream comprising hydrogen and at least about 20 to 60 mole % $C_2$–$C_5$ olefinic hydrocarbons; cooling the effluent to a temperature of less than about −200° F. by indirect heat exchange with the admixture; passing the effluent to a first vapor-liquid separation zone and recovering therefrom a hydrogen-containing vapor phase and a liquid phase comprising at least about 20 to 60 mole % $C_2$–$C_5$ olefinic hydrocarbons; passing the hydrogen-containing vapor phase into indirect heat exchange with a hydrogen-rich gas; contacting the hydrogen-containing vapor phase with a lean liquid absorbent comprising at least about 20 to 60 mole % $C_2$–$C_5$ paraffinic hydrocarbons at a temperature of less than about −250° F. in a countercurrent liquid absorption zone to produce the hydrogen-rich gas stream and a methane-rich liquid absorbent; refrigerating the hydrogen-rich gas stream to a temperature of less than about −280° F. and passing the refrigerated hydrogen-rich gas stream in indirect heat exchange with the hydrogen-containing vapor phase; admixing the hydrogen-rich gas stream with a hydrocarbon liquid comprising 20 to 60 mole % $C_2$–$C_5$ paraffinic hydrocarbons to form the admixture; and recycling at least a portion of the admixture to the dehydrogenation zone.

BRIEF DESCRIPTION OF THE DRAWING

The accompanying FIGURE is a schematic flow diagram of one embodiment of the present invention.

DETAILED DESCRIPTION OF THE PREFERRED EMBODIMENT

The feedstock for the dehydrogenation reaction zone of the present invention is an admixture of hydrogen and $C_2$–$C_5$ paraffinic hydrocarbons. Suitable $C_2$–$C_5$ hydrocarbons include ethane, propane, butane and pentane, and any mixtures or isomers thereof. In a preferred embodiment, the feedstock comprises less than about 2 mole % $C_6+$ hydrocarbons. A suitable hydrogen to hydrocarbon mole ratio is about 0.1:1 to 40:1, preferably about 0.4 to 1.0.

The hydrocarbon feedstock of the present invention can be pretreated to remove impurities such as water, organic nitrogen, metals, and sulfur compounds that are harmful to the dehydrogenation catalyst. This pretreatment usually consists of directing the feed stream through at least one guard bed containing activated alumina.

The $C_2$–$C_5$ paraffinic hydrocarbon feedstock is introduced into a dehydrogenation section having at least one reactor that converts these paraffins to olefins in the presence of a dehydrogenation catalyst.

Any suitable dehydrogenation catalyst may be used in the process of the present invention. Generally, the preferred catalyst comprises a platinum group metal component, an alkali metal component and a porous inorganic oxide material. The catalyst may also contain promoter metals which advantageously improve the performance of the catalyst. It is preferable that the porous carrier material of the dehydrogenation catalyst be an absorptive high surface area support having a surface area of about 25 to about 500 m²/g. The porous carrier material should be relatively refractory to the conditions utilized in the reaction zone and may be chosen from those carrier materials which have traditionally been utilized in dual function hydrocarbon conversion catalysts. A porous carrier material may therefore be chosen from activated carbon, coke, or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxide, magnesia, silica alumina, alumina boria, crystalline alumina silicates or a combination of one or more of these materials. The preferred porous carrier material is a refractory inorganic oxide, with the best results being obtained with an alumina carrier material, particularly gamma alumina. In a preferred embodiment, the catalyst is a spherically-shaped gamma alumina carrier having a diameter of about 1/16".

The preferred dehydrogenation catalyst also contains a platinum group metal component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., of an elemental metal, or in combination with one or more other ingredients of the catalyst. It is believed that the best results are obtained when substantially all of the platinum group components exist in the elemental state. The platinum group component generally comprises from about 0.1 to about 2 wt. % of the final composite, calculated on an elemental basis. It is preferred that the platinum content of the catalyst be between about 0.2 and 1 wt. %. The preferred platinum group component is platinum, with palladium being the next preferred metal.

The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to an impregnated carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium and lithium. The preferred alkali metal is normally either potassium or lithium, depending on the feed hydrocarbon. The concentration of alkali metal may range from about 0.1 to 3.5 wt. %, but is preferably between 0.2 and about 2.5 wt. % calculated on an elemental basis. This component may be added to the catalyst by the methods described above as a separate step or simultaneously with the solution of another component.

As previously noted, the dehydrogenation catalyst may also contain promoter metal. One such preferred promoter is tin. The tin component should constitute about 0.01 to about 1 wt. % tin. It is preferred that the atomic ratio of tin to platinum be between 1:1 and 6:1. The tin component may be incorporated into the catalytic composite in any suitable manner known to effectively disperse this component in a very uniform manner throughout the carrier material. Thus, the component may be added to the carrier material by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component to the carrier material may be obtained by reference to U.S. Pat. No. 3,745,112.

The dehydrogenation catalyst may be employed in the dehydrogenation reactor as a fixed bed, fluidized bed, or a moving bed. Moreover, the dehydrogenation catalytic reactor may contain multiple catalyst beds. In one such system, the catalyst is employed within an annular bed through which it is movable via gravity flow. In such a system, there are typically a plurality of reactors in series. It is common practice to remove the catalyst from the bottom of the last reactor, regenerate the catalyst, then return the catalyst to the top of the reactor.

The operating conditions employed in the dehydrogenation reactor will vary depending upon such factors as catalyst activity, feedstock and desired conversion. A general range of conditions which may be employed for dehydrogenation of a light hydrocarbon include a temperature of from about 1022° F. to about 1472° F., a pressure from about 0.01-10 atmospheres absolute, a liquid hourly space velocity between about 0.1-100 $hr^{-1}$ and a hydrogen to hydrocarbon mole ratio from about 0.01:1 to about 40:1.

Upon removal of the dehydrogenation effluent from the last reactor in the dehydrogenation zone, it is cooled by indirect heat exchange typically with the hydrogen/hydrocarbon admixture that is used for feed to the dehydrogenation reactor. The dehydrogenation effluent is then further cooled usually with air or cooling water to a temperature of about 100° F. The dehydrogenation effluent is then compressed to 60-200 psig. That compressor effluent is then cooled usually with air or cooling water to about 100° F. and then directed to a contaminant removal zone to remove such components as HCl, $H_2S$ and water.

The dehydrogenation effluent exits the dehydrogenation section and enters a first means for indirect heat exchange with the dehydrogenation feed stream. The preferred first heat exchanger means is a plate-fin heat exchanger. A plate-fin heat exchanger is a tubeless vessel that contains a plurality of separate adjacent compartments for the flow of process fluids (usually in the opposite direction). Although the process of the present invention is described herein with respect to a particular process stream passing through the plate-fin heat exchanger and coming into indirect heat exchange with another process stream, the present invention is not intended to exclude the presence of other process streams simultaneously passing through the plate-fin heat exchanger and coming into indirect heat exchange therewith. Extending from the inner walls of these compartments is a plurality of fins that promote heat transfer from fluids flowing in adjacent compartments. Passing the dehydrogenation effluent into this first plate-fin heat exchanger lowers the temperature of the dehydrogenation effluent from about 100° F. entering the first plate-fin heat exchanger to about 10° to −150° F. exiting the first plate-fin heat exchanger.

Following the indirect heat exchange step, the dehydrogenation effluent is passed to a first vapor-liquid equilibrium separation zone, thereby producing a liquid phase comprising $C_2-C_5$ olefinic hydrocarbons and a hydrogen-containing vapor phase. The first vapor-liquid equilibrium separation zone is maintained at a temperature of less than about 10° to −150° F. and a pressure of about 100 psig.

The liquid phase preferably comprises at least about 20-70 mole % of the olefinic hydrocarbons and unreacted paraffins contained in the reactor effluent. In a preferred embodiment, at least a portion of the liquid phase is passed to a second vapor-liquid equilibrium separation zone to produce a methane-rich overhead that may be rich in hydrogen and light hydrocarbons and a hydrocarbon liquid product stream of reduced vapor pressure. The second vapor-liquid equilibrium separation zone can be operated at a temperature of about 10° to −150° F. and pressure of about 5 psig. The overhead stream can be sent back to the dehydrogenation zone, in particular the suction end of the reactor effluent compressor. This enables the second vapor-liquid separator to be operated at a lower vapor pressure. Also recycling this overhead stream back to the dehydrogenation section reduces product losses.

The liquid hydrocarbon product stream comprises predominantly $C_2-C_5$ olefinic hydrocarbons and unreacted paraffinic hydrocarbons. This liquid hydrocarbon product stream can be passed into a pump that increases the pressure of the liquid product stream to about 200-300 psig. After exiting the pump, the liquid hydrocarbon product stream can be passed into indirect heat exchange with the dehydrogenation effluent at the first plate-fin heat exchanger. As a result, the temperature of the liquid hydrocarbon product stream can be raised to about 80° F. The liquid hydrocarbon product stream can be recovered or sent downstream for further processing, such as fractionation.

The hydrogen-containing vapor phase resulting from the first vapor-liquid separator is a relatively impure hydrogen gas stream containing significant amounts of low molecular weight hydrocarbons, e.g., methane and ethane. The hydrogen-containing vapor phase has a hydrogen concentration of about 80 mole %.

In a preferred embodiment of the present invention, the hydrogen-containing vapor phase is passed to a second plate-fin heat exchanger for additional indirect heat exchange prior entering the next separation stage. This second plate-fin heat exchanger reduces the temperature of the hydrogen-containing vapor phase to about −150° to −250° F.

In accordance with the present invention, the hydrogen-containing vapor phase is contacted in a cold absorption zone with a lean liquid absorbent comprising $C_2-C_5$ hydrocarbons, preferably $C_2-C_5$ paraffinic hydrocarbons. As previously mentioned, the present invention contacts the hydrogen-containing vapor phase with the lean liquid absorbent under very cold conditions. Accordingly, the temperature of the cold absorption zone is maintained at less than about −120° F., preferably less than about −200° F., most preferably less than about −250° F. A suitable operating pressure for the cold absorption zone can be about 100 psig.

In a preferred embodiment, the hydrogen-containing vapor phase and the liquid absorbent are contacted in a countercurrent absorption zone, i.e., the upflowing vaporous materials of the hydrogen-containing vapor phase are intimately contacted in a countercurrent fashion with a descending stream of the liquid absorbent. Accordingly, in the countercurrent absorption zone, a relatively impure hydrogen-containing gas stream containing significant amounts of low molecular weight hydrocarbons passes upwardly through a plurality of contacting stages and the hydrocarbon portions of which are selectively absorbed by the downwardly passing relatively heavy hydrocarbons contained in the lean liquid absorbent.

The products of the absorption zone are a methane-rich absorber liquid (containing most of the hydrocarbons in the hydrogen-containing vapor stream) and a hydrogen-rich gas stream. In a preferred embodiment, the methane-rich absorber liquid is passed to the second plate-fin heat exchanger for indirect heat exchange (which increases the temperature of the methane-rich absorber liquid to about −120° F.) and directed to a third vapor-liquid equilibrium separation zone that is operated at a pressure of about 20 to 50 psig. An overhead vapor stream rich in methane exits the top of the third vapor-liquid separation zone. This overhead stream can be passed to the first plate-fin heat exchanger and may be compressed, if necessary, to enter an existing fuel gas system.

Exiting the bottom of the third vapor-liquid equilibrium separation zone is the lean liquid absorbent that can be recycled to the cold absorption zone. In a preferred embodiment, the lean liquid absorbent is pumped into a second plate-fin heat exchanger for indirect heat exchange prior to being recycled to the absorption zone.

In accordance with the present invention, the hydrogen-rich gas stream exits the top of the absorption zone and is subjected to refrigeration. Any suitable refrigeration means known to those skilled in the art may be employed. In a preferred embodiment, the means for refrigerating the hydrogen-rich gas stream is gas expansion with shaft work that removes energy. In this gas expansion mode, the hydrogen-rich gas stream enters a gas expander having a generator with a common shaft between the generator and the gas expander. The hydrogen-rich gas stream enters the gas expander at a pressure of about 60–200 psig causing the turbine to rotate (similar to the operation of a pinwheel). This in turn causes the shaft to rotate, thereby removing work energy from the hydrogen-rich gas stream and reducing the temperature of the hydrogen-rich gas stream from about −150° F. to about −280° F. The relatively high pressure drop across the gas expander causes the hydrogen-rich gas stream to exit the expander at a pressure of about 40 psig.

After refrigeration, the hydrogen-rich gas stream is preferably passed to the second plate-fin heat exchanger for indirect heat exchange. Such heat exchange increases the temperature of the hydrogen-rich gas stream to a temperature of about 10° to −125° F.

The hydrogen-rich gas stream can then be split into two streams, a net hydrogen stream and a hydrogen recycle stream. In a preferred embodiment, the net hydrogen stream is directed to the first plate-fin heat exchanger for indirect heat exchange prior to use in other hydrocarbon conversion processes located in the refinery.

The hydrogen recycle stream can be admixed with the hydrocarbon liquid component of the dehydrogenation feed stream. In a preferred embodiment, the hydrocarbon liquid is passed to the first plate-fin heat exchanger for indirect heat exchange prior to admixing with the hydrogen recycle gas. After admixing, the admixture can be passed to the first plate-fin heat exchanger prior to being routed to the dehydrogenation section of the present invention.

The further description of the process of this invention is presented with reference to the attached drawing. The drawing represents one preferred embodiment of the invention and is not intended as an undue limitation on the generally broad scope of the invention as set out in the appended claims.

Referring to the drawing, a hydrocarbon feed stream comprising $C_2$–$C_5$ paraffinic hydrocarbons enters a first aluminum plate-fin heat exchanger 14 via line 2 at a temperature of about 100° F. After exiting the heat exchanger 14 by line 3 at temperature of about −120° F., the hydrocarbon feed stream is admixed with a recycle hydrogen stream via line 11 to form an admixture feed stream 8. This admixture feed stream enters the heat exchanger 14 at line 8 at a temperature of about −122° F. and exits the heat exchanger 14 by stream 1 at a temperature of about 80° F. After exiting the heat exchanger 14, the heated admixture feed stream enters the dehydrogenation section 4 via line 1.

Although in the figure the dehydrogenation section 4 is shown only as a single box, it consists of at least one dehydrogenation reactor and an assortment of pre-reactor heat exchangers, pre-reactor activated aluminum beds for removing impurities, interstage heaters and post-reactor coolers (all not shown). Also included in the dehydrogenation section 4 is at least one dehydrogenation effluent compressor (not shown) that increases the pressure of the effluent up to about 100 psi.

In any event, a compressed, effluent stream exits the dehydrogenation section 4 via line 12 at a temperature of about 100° F. and a pressure of about 100 psi. This effluent stream entering at line 12 is then routed to the first plate-fin heat exchanger 14 and is therein passed into indirect heat exchange with the previously mentioned feed stream admixture which enters the heat exchanger 14 via line 8.

After exiting the heat exchanger 14, the compressed, cooled effluent is introduced via stream 16 to a high pressure vapor-liquid separator 22. The vapor-liquid separator is operated at a temperature of about −120° F. and a pressure of about 100 psig. Exiting the bottom of the separator 22 in stream 24 is a liquid phase comprising a substantial amount of $C_2$–$C_5$ olefinic hydrocarbons as well as unreacted paraffinic hydrocarbons. This liquid phase 24 is then passed to a low pressure vapor-liquid separator 26 that operates at a pressure of less than about 5 psig. Exiting the top of the low pressure separator 26 in line 25 is a stream comprising hydrogen and light hydrocarbons. The overhead stream then enters the first plate-fin heat exchanger 14 at line 25 where it is passed into indirect heat exchange with the dehydrogenation section effluent stream 12. Exiting the first plate-fin heat exchanger 14 at line 27, the heated overhead stream, having a temperature of about 80° F., is then recycled to the dehydrogenation section 4.

Exiting the bottom of the low pressure separator 26 in stream 30 at a temperature of about −120° F. is a liquid product stream 30 comprising predominantly $C_2$–$C_5$ olefinic hydrocarbons as well unreacted paraffinic hydrocarbons. This liquid product stream is then passed via stream 30 into a liquid product pump 31 that increases the pressure of the liquid product stream to about 200-300 psig. After exiting the liquid product pump 31 by line 33, the compressed, liquid product stream is passed into the first plate-fin heat exchanger 14 where it is brought into indirect heat exchange with the dehydrogenation effluent 12. As a result, the temperature of the liquid product stream is raised to about 80° F. The liquid product stream exits the heat exchanger 14 at line 35 and is sent downstream for further processing, such as fractionation.

A hydrogen-containing vapor phase exits the high pressure separator 22 via line 34 and is passed to a second plate-fin heat exchanger 36 where the hydrogen-containing vapor phase is passed in indirect heat exchange with a hydrogen-rich gas stream which enters the heat exchanger 36 at line 57. The hydrogen-containing vapor phase enters the second plate-fin heat exchanger 36 at stream 34 at a temperature of about −120° F. and exits the plate-fin heat exchanger 36 via stream 37 at a temperature of less than about −250° F.

The cooled, hydrogen-containing vapor phase is then introduced into the bottom of a cold absorber column 38 by line 37. Near the top of the absorber column 38, a lean liquid absorbent stream comprising $C_2-C_5$ paraffinic hydrocarbons and a small amount of methane is introduced by line 45 in a fashion countercurrent to the flow of the hydrogen-containing vapor phase at a temperature of about −250° F. and a pressure of about 100 psi. A methane-rich liquid absorbent exits the bottom of the absorber column 38 via line 42 at temperature of less than about −250° F. and is passed to the second plate-fin heat exchanger 36 where it is brought into indirect heat exchange with the hydrogen-containing vapor phase.

The methane-rich liquid absorbent exits the bottom of second plate-fin heat exchanger 36 at a temperature of less than about −120° F. via line 44 and enters an intermediate pressure vapor-liquid separator 46 where a methane-rich gas stream is removed overhead via line 48. The intermediate pressure separator 46 operates at a pressure of about 20 psig. The methane-rich gas stream is then introduced to first plate fin heat exchanger 14 via line 48 wherein it is passed into indirect heat exchange with an effluent stream from the dehydrogenation section of the present invention. A warmed, methane-rich gas stream exits the first plate heat exchanger 14 via stream 60 and is directed to the fuels section of the refinery.

The lean liquid absorbent exits the intermediate pressure vessel 46 at a temperature of less than about −120° F. by line 40. The liquid absorbent is then introduced to a lean liquid absorbent pump 39 that increases the pressure of the lean liquid absorbent from about 20 psig to about 100 psig. The lean liquid absorbent exits the pump 39 via line 43 and is passed to the second plate-fin heat exchanger 36 wherein it is brought into indirect heat exchange with the methane-rich liquid absorbent. As a result, the temperature of the cooled liquid absorbent is lowered from about −120° F. to about −250° F. The cooled liquid absorbent is then directed back to the top the absorber 36 via stream 45.

A hydrogen-rich gas stream exits the top of the absorber column 38 via line 54 and is transferred to a gas expander 56. Exiting the gas expander 26 at a temperature of about −280° F. and a pressure of about 40 psi via stream 57, the hydrogen-rich gas stream is directed to the second plate-fin heat exchanger 36 wherein the hydrogen-rich gas stream is passed into indirect heat exchange with the hydrogen-containing vapor phase. The hydrogen-rich gas stream exits the plate-fin heat exchanger 36 via line 6 at a temperature of about −125° F.

At junction 7, the hydrogen-rich gas stream is split into two separate stream, the net hydrogen stream 9 and the recycle hydrogen stream 11. The net hydrogen stream is subsequently passed to the first plate-fin heat exchanger 36 prior to being sent to other hydrocarbon conversion processes located in the refinery via line 61. The recycle hydrogen stream 11 is then admixed with the cooled, hydrocarbon liquid stream 3 to form the admixture 8. The admixture 8 is then passed to the first plate-fin heat exchanger 14 for indirect heat exchange with the dehydrogenation effluent stream. The heated admixture exits the first plate-fin heat exchanger 14 in stream 1 and is then directed to the dehydrogenation section 4.

What is claimed:

1. A process for producing a hydrogen/hydrocarbon admixture for use in a catalytic dehydrogenation reaction zone by treating an effluent of said dehydrogenation zone, said effluent comprising at least about 20 to 60 mole % $C_2-C_5$ olefinic hydrocarbons, comprising the steps of:
   (a) cooling said effluent by indirect heat exchange with said admixture;
   (b) passing said effluent to a first vapor-liquid separation zone and recovering therefrom a hydrogen-containing vapor phase comprising methane and a liquid phase comprising $C_2-C_5$ olefinic hydrocarbons;
   (c) contacting said hydrogen-containing vapor phase with a lean liquid absorbent comprising $C_2-C_5$ hydrocarbons at a temperature of less than about −120° F. in a countercurrent absorption zone to produce a hydrogen-rich gas stream and a methane-rich liquid absorbent;
   (d) refrigerating said hydrogen-rich gas stream to a temperature of less than about −200° F. to recover high purity hydrogen and passing said refrigerated, hydrogen-rich gas stream in indirect heat exchange with said hydrogen-containing vapor phase;
   (e) admixing said hydrogen-rich gas stream from step (d) with a hydrocarbon liquid comprising $C_2-C_5$ paraffins to form said admixture; and
   (f) recycling at least a portion of the admixure to said dehydrogenation zone.

2. The process of claim 1 wherein said absorption zone is operated at a temperature of less than about −250° F.

3. The process of claim 1 further comprising passing said liquid phase in step (b) to a second vapor-liquid separation zone to produce a methane-rich overhead stream and a hydrocarbon liquid product stream.

4. The process of claim 3 further comprising passing said methane-rich overhead stream in indirect heat exchange with said dehydrogenation effluent.

5. The process of claim 3 further comprising passing said hydrocarbon liquid product stream in indirect heat exchange with said dehydrogenation effluent.

6. The process of claim 1 further comprising passing said methane-rich liquid absorbent from step (c) to a third vapor-liquid separation zone to produce said lean liquid absorbent, 7. The process of claim 6 further comprising passing said lean liquid absorbent into indirect heat exchange with said methane-rich, liquid absorbent.

* * * * *